(12) United States Patent
Walker et al.

(10) Patent No.: US 11,833,106 B2
(45) Date of Patent: *Dec. 5, 2023

(54) AUTOMATIC DETERMINATION OF DEFIBRILLATION PAD LOCATION ON PATIENT'S CHEST

(71) Applicant: Physio-Control, Inc., Redmond, WA (US)

(72) Inventors: Robert G. Walker, Seattle, WA (US); Robert P. Marx, Jr., Kent, WA (US)

(73) Assignee: Physio-Control, Inc., Redmond, WA (US)

( * ) Notice: Subject to any disclaimer, the term of this patent is extended or adjusted under 35 U.S.C. 154(b) by 1143 days.

This patent is subject to a terminal disclaimer.

(21) Appl. No.: 16/544,510

(22) Filed: Aug. 19, 2019

(65) Prior Publication Data

US 2019/0365600 A1 Dec. 5, 2019

Related U.S. Application Data

(63) Continuation of application No. 15/052,776, filed on Feb. 24, 2016, now Pat. No. 10,383,789.

(51) Int. Cl.
*A61H 31/00* (2006.01)

(52) U.S. Cl.
CPC .......... *A61H 31/005* (2013.01); *A61H 31/007* (2013.01); *A61H 2203/0456* (2013.01); *A61H 2205/084* (2013.01)

(58) Field of Classification Search
CPC ................ A61H 31/005; A61H 31/007; A61H 2203/0456; A61H 2205/084; A61H 2201/1619; A61H 31/00; A61H 31/006; A61H 2031/002; A61H 2201/1253; A61H 2201/1669; A61H 2201/1688; A61H 2201/5007; A61H 2201/5043; A61H 2201/5097; A61H 2230/82; A61H 1/00; A61N 1/046; A61N 1/39044; A61N 1/39046

See application file for complete search history.

(56) References Cited

U.S. PATENT DOCUMENTS

| 10,383,789 B1 * | 8/2019 | Walker .................. A61H 31/00 |
| 2012/0083720 A1 | 4/2012 | Centen et al. |
| 2013/0225972 A1 | 8/2013 | Banville et al. |
| 2013/0296747 A1 * | 11/2013 | Perreault .............. A61H 31/005 601/41 |
| 2014/0046228 A1 | 2/2014 | Walker |
| 2014/0163436 A1 | 6/2014 | Peterson et al. |
| 2015/0164417 A1 | 6/2015 | Tupin, Jr. |

OTHER PUBLICATIONS

Office Action for U.S. Appl. No. 15/052,776, dated May 31, 2018, Walker, "Automatic Determination of Defibrillation Pad Location on Patient's Chest," 8 pages.

* cited by examiner

*Primary Examiner* — Quang D Thanh
(74) *Attorney, Agent, or Firm* — Lee & Hayes P.C.

(57) ABSTRACT

A medical device uses UWB units to infer a position of an adjunct positioned in proximity to an exterior portion of a patient's body. The position information can be used to provide CPR feedback to a rescuer. In other applications, the position information can be used to provide prompts to a user to change the position of the adjunct.

19 Claims, 5 Drawing Sheets

FIG. 1

COMPRESSION STRUCTURE OF CPR
CHEST COMPRESSION MACHINE

METHODS

FIG. 4

METHODS

FIG. 5

AUTOMATIC DETERMINATION OF DEFIBRILLATION PAD LOCATION ON PATIENT'S CHEST

CROSS-REFERENCE TO RELATED APPLICATIONS

This application is a continuation of U.S. patent application Ser. No. 15/052,776, entitled "AUTOMATIC DETERMINATION OF DEFIBRILLATION PAD LOCATION ON PATIENT'S CHEST", and filed on Feb. 24, 2016, which will issue on Aug. 20, 2019 as U.S. Pat. No. 10,383,789, the contents of which are incorporated by reference herein in their entirety.

BACKGROUND

In certain types of medical emergencies, Cardiopulmonary Resuscitation (CPR) needs to be delivered to a patient. CPR includes repeatedly compressing the chest of the patient, to cause their blood to circulate some. CPR also includes delivering rescue breaths to the patient. A number of people are trained in CPR, just in case, even though they are not trained in the medical professions.

The chest compressions are intended to cause the blood to continue circulating, so as to prevent damage to organs like the brain. In some instances, the chest compressions merely maintain the patient, until a more definite therapy is made available, such as defibrillation. Defibrillation is an electrical shock deliberately delivered to a person, in the hope of correcting their heart rhythm.

A problem is that CPR is sometimes ineffective at providing blood circulation to the patient. That can happen whether or not the rescuer who performs the CPR is part of the medical profession. The most frequent example of such ineffectiveness is compressions that are not deep enough, or not frequent enough, or do not last long enough. Even the best trained rescuers can become fatigued after delivering CPR, with the compressions deteriorating in quality. And that is without even accounting for the emotions of the moment, which might impact a lay rescuer.

The risk of ineffective chest compressions has been addressed with CPR feedback devices, some of which are standalone, while others are integrated or cooperate with defibrillators. These devices actually detect the depth and frequency of compressions that the rescuer is performing, and give feedback to the rescuer that is specifically attuned to what the rescuer is doing. This feedback is in accordance with how well the rescuer is meeting guidelines, such as those of the American Heart Association. These prompts and other instructions and can help the rescuer focus, even if the latter cannot remember their training.

Reaching the appropriate depth is difficult. The recommended depth is a range. If the actual depth is less than the range, not enough blood is moved within the patient. If the depth exceeds the range, the patient's ribs may break. And, even for experienced rescuers, it is sometimes hard to discern the appropriate depth. Reaching the appropriate depth is even more difficult if the patient is on a flexible mattress that partly recedes, as the rescuer is pushing from the top. And CPR compressions can be even more challenging if the rescuer has to deliver them in a moving ambulance.

An alternative to manual CPR are CPR chest compression machines. Such machines have been known by a number of names, such as mechanical CPR devices, cardiac compressors, external chest compression machines, and so on. One such machine is the LUCAS® available from Physio-Control, Inc., Redmond, Wash.

CPR chest compression machines repeatedly compress and release the chest of the patient. Such machines can be programmed so that they will compress and release at the recommended rate, and to a specific depth within the recommended range. Some CPR chest compression machines have a rigid back plane upon which the patient is placed in a supine position.

BRIEF SUMMARY

In one embodiment, a medical device includes an ultra-wide band (UWB) transmit/receive device (hereinafter UWB unit), and a processor configured to process signals from the UWB unit when the UWB unit transmits UWB signals into a patient. In one application, for example, the patient has adjunct(s) attached to his or her body while being monitored or undergoing a therapy. The UWB signals transmitted into the patient's body can be reflected by the adjunct(s) so that at least some portion is received by the UWB unit. The received portion of the reflected UWB signal can be processed to determine the location of the adjunct(s). In some applications, this information is used to determine the compression depth of CPR being performed on the patient. In other applications, this information is used to determine whether the adjunct(s) are properly positioned on the patient.

In some implementations, the UWB unit is disposed in the back plate of a CPR chest compression machine, or in a component of a CPR feedback device used for manual CPR.

DETAILED DESCRIPTION

In one embodiment, a system for monitoring and/or providing feedback on chest compression depth, and other associated parameters, incorporating: one or more UWB units, and accompanying adjunct(s) placed on a patient's chest that move as the patient's chest is moved during CPR. In one possible implementation, an adjunct is placed beneath the hands of the rescuer providing chest compressions during CPR.

The UWB unit detects and tracks the position of the phantom, allowing determination of chest height and compression depth. Because the phantom requires no electronics and can be achieved with only a thin layer of suitable material, the invention allows for a rescuer's hands to be placed in the traditional manner directly on the patient's chest, without the thickness/awkwardness of an intervening "puck".

Figure 1:
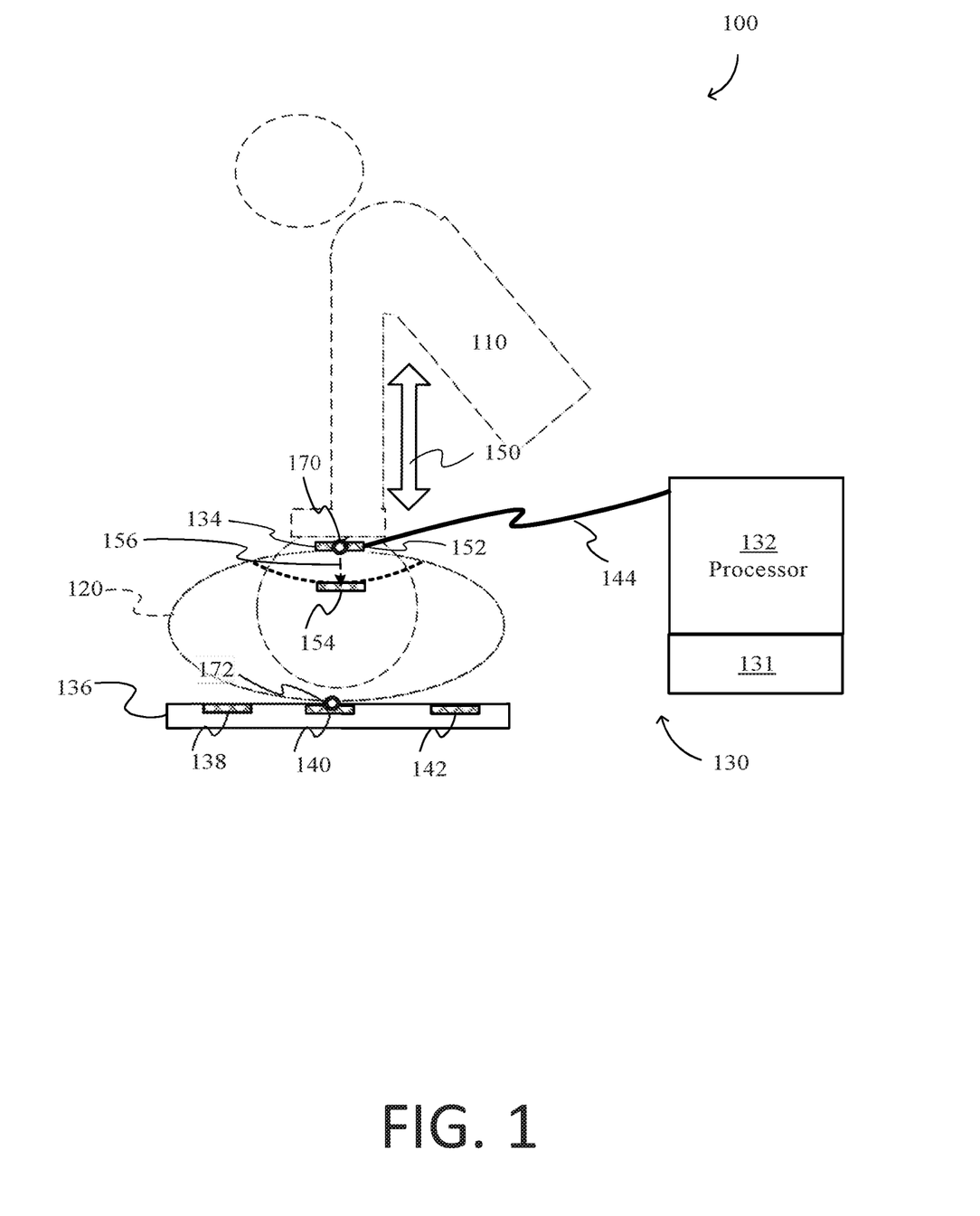
FIG. 1 illustrates a Cardiopulmonary Resuscitation (CPR) chest compression scenario in which a standalone medical device may be employed in accordance with the technology described herein according to various embodiments.

FIG. 1 shows a CPR scene 100 with a rescuer 110 resuscitating a patient 120 using CPR chest compressions. The scene 100 also includes a standalone medical device 130 that is designed to assist with CPR chest compression resuscitation. The medical device 130 includes a processor 132, an adjunct 134, and backboard 136 with one or more UWB units. In this particular embodiment, the medical device includes UWB units 138, 140, and 142. Alternately, these UWB units may be attached to the patient's body, such as in the back.

In another embodiment, a UWB unit is embedded or attached to adjunct 134, and backboard 136 includes reflector elements (not shown) instead of the UWB units 138, 140, and 142. These reflector elements are sometimes referred to herein as phantoms.

The medical device 130 includes an output unit 131. In embodiments in which a UWB unit is embedded or attached to adjunct 134, the processor 132 is connected to the UWB unit in adjunct 134 via wires 144. In embodiments in which the UWB unit(s) is in the backboard 136, the processor wires 144 would be connected to the UWB units in the backboard 136. Alternatively, these components maybe connected wirelessly.

UWB technology is well known, and in the medical field has been described and developed for various physiologic imaging and diagnostic purposes. In the specific field of cardiac arrest resuscitation, UWB has been disclosed and explored for the detection of mechanical heart motion indicative of a pulse. These applications involve use of the UWB technology for physiologic monitoring (e.g. cardiac motion, lung motion, etc.). However, Applicants have not found any disclosures related to application of the UWB technology for monitoring the behavior and motion of a medical provider attending to the patient, or monitoring things that are placed on, or lie outside of, the patient's body. More specifically, in one application, the embodiment uses UWB technology to measure in "real time" the displacement of the patient's chest during CPR. In one embodiment, the UWB unit transmits a series of pulses and measures the time of flight of each one. The processor then converts the time measurement into a distance. By making a series of such distance determinations, the medical device can provide an indication (e.g., via the display unit 131) of the compressions and releases performed by the rescuer.

With the example medical device 130, in one embodiment the UWB technology determines the depth of a CPR compression based, at least in part, upon two points. One point is the adjunct 134 on the patient's chest and another point is the backboard 136 (or the patient's back). These points are illustrated in FIG. 1 as front point 170 and back point 172.

The UWB units 138, 140 or 142 will transmit wireless UWB signals through the body of patient 120 toward adjunct 134. Note, in light of this disclosure, those of skill in the art will appreciate that other embodiments can use a single UWB unit. For multiple UWB unit embodiments, each UWB unit may transmit a different wavelength from the other units. The wireless signals will be reflected at least in part by the adjunct 134. The UWB units are arranged to receive the reflections, and in this embodiment, determine the time it took for the transmitted signal to reach the adjunct 134 and return to the UWB unit after the reflection. Processor 132 can then process theses times to determine a single measure of distance from the back point 172 to the front point 170.

To increase the signal strength of the reflections, the adjunct 134 can include a phantom. A phantom as used herein is a material designed to create a distinct reflected signal for use with imaging systems such as ultrasound or UWB. For RF signals, metal provides excellent reflectivity. RF propagates reasonably well through human tissue, such that a thin film of metal should be more than adequate to create a distinct reflected signal suitable for tracking by the UWB units. Thus the RF phantom would have one or more of the following characteristics: 1) The phantom could be part of a thin, flexible film/pad of foil or similar metal content; The phantom could be a small metallic pattern of distinct shape (such as concentric circles, etc.), within a larger film/pad, such that the UWB unit(s) could readily identify the shape as the tracking target, and distinguish it from any other reflecting surfaces seen in the environment; 3) The film/pad containing the phantom could have an adhesive surface on one side, so that it can stick to and stay properly positioned on the patient's chest (graphics/labeling on the opposite site could help the rescuer properly position the pad); 4) The film/pad containing the phantom could be disposable; 5) The film/pad could be doped with material to modify the reflected spectral signature. This could be used to uniquely identify it from surrounding materials; 6) The film/pad could additionally be designed to provide electrical insulation, such that the rescuer could safely have their hands on the patient's chest during an external defibrillation shock without risk of defibrillation current flowing from the patient's chest into the rescuer's hands; 7) The phantom material/signature could additionally be incorporated into the gloves worn by the rescuer, allowing separate tracking of both the phantom pad attached to the patient's chest, and the hands of the rescuer. Identifying separation of the hands off of the pad would provide an indication that full chest recoil was achieved. While a lack of separation between the rescuer's hands and the chest pad does not necessarily imply lack of full chest recoil, it is noteworthy that some methods of training chest compression technique teach that the hands should separate from the chest after each compression. Thus tracking the rescuer's hands separately from the chest pad, and identifying separation between the two targets, could provide a useful measure of compliance with desired good chest compression technique.

During CPR, the patient 120 is placed on the backboard 136 and the adjunct 134 is placed onto or in very close proximity to the patient's chest. Often, the adjunct has an adhesive for temporary attachment to the patient's chest. In this situation, the adjunct 134 defines the front point 170 that corresponds to the patient's chest. Similarly, the backboard defines the back point 172 that corresponds to the back of the patient 120.

With his hand to the chest of the patient 120, the rescuer 110 pumps the patient's chest. The up and down motion of the compression and releases is represented by double-headed arrow 150. Note that the arrow 150 indicates that the compressions are in the center of the patient's chest.

When compressions 150 are performed on the patient 120, the adjunct 134 on the patient's chest moves from a first position 152 to a position 154. Arrow 156 indicates the direction of the chest compression and the depth of compression. The depth of compression is the distance that the adjunct 134 travels when it moves from position 152 to position 154 can be correlated to a depth of compression. The indications may be provided to the rescuer real-time or collected to allow the rescuer to review them later.

According to the 2010 CPR Guidelines from the American Heart Association, the desired for depth of compression for a typical adult is at least two inches. For a typical child, it is at least a third of the depth of the chest. Of course, the exact right distance depends upon the chest cavity size of the actual patient.

The processor 132 is coupled to the UWB units at backboard 136. One or more of the UWB units transmit a UWB signal to the adjunct. The adjunct 134 reflects the signal(s) from the UWB units at backboard 136.

Based at least in part on the reflected UWB signal(s), the processor 132 determines the depth of compression of the compressions 150 during delivery of the CPR chest compression.

The output unit 131 may communicate a recommended additional CPR chest compression and that such compression be done at a different depth.

Integrating the constellation of UWB units 138, 140, and 142 in the backboard 136 allows a fixed reference for inferring the position of the top of the chest during CPR. While not necessary, the constellation of UWB units 138, 140, and 142 in some embodiments is further placed in the backboard 136 in a spatially repeating pattern.

Each UWB unit 138, 140, and 142 can be encoded with its location relative to the backboard 136 or equivalent portion of the backboard 136, and also as to its location relative to the other UWB units 138, 140, and 142 in the constellation.

Determination can be by a suitable mathematical operation, such as triangulation. This procedure can be done at a high sample rate as to track the motion of the reader through space as compressions are being performed.

The processor 132 determines the depth of CPR chest compression during delivery of the CPR chest compression. Based on the time measurements from UWB units 138, 140, and 142, the processor 132 can determine the distance from the adjunct 134 to a selected UWB unit, and optionally also to each other UWB unit in the constellation of UWB units 138, 140, and 142.

In one or more implementations, the disclosed UWB technology determines the depth of a CPR compression delivered by the rescuer 110. For example, in embodiments a system for the processor 132 detects the distance many times per second to detect the motion of the adjunct 134 during CPR.

Figure 2:
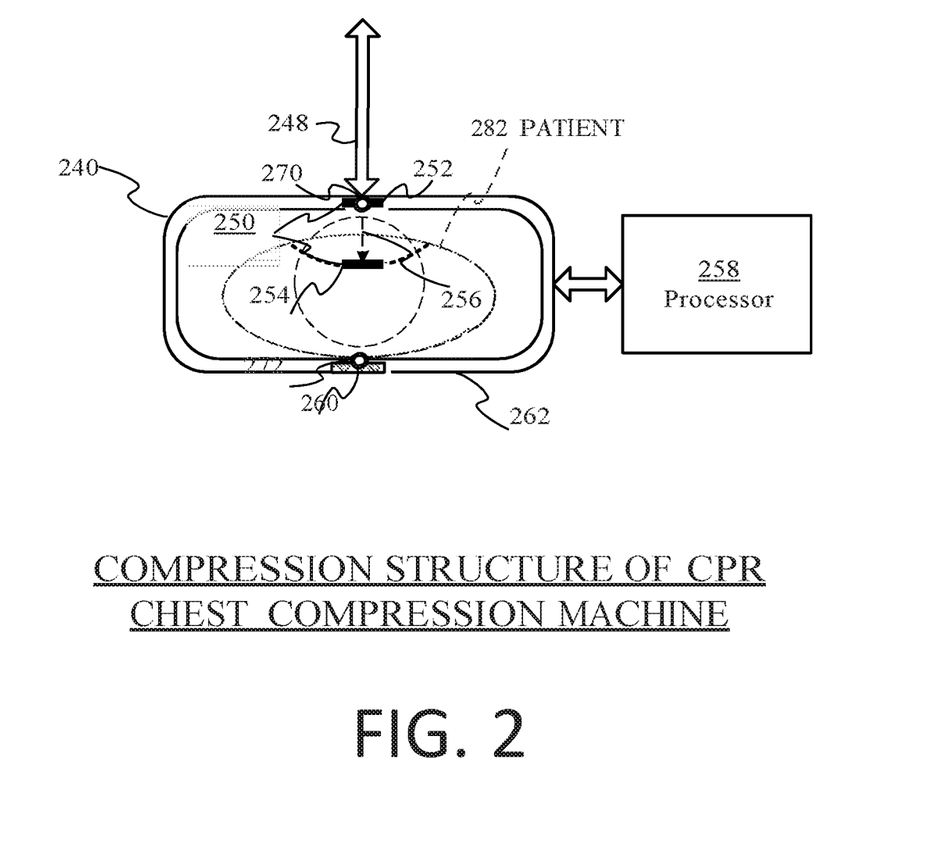
FIG. 2 is a diagram of an abstracted compression structure of a Cardiopulmonary Resuscitation (CPR) chest compression structure used to save the life of a person in accordance with the technology described herein.

FIG. 2 is a diagram of an abstracted compression structure 240 of a CPR chest compression structure according to the technology described herein. A patient 282 is placed within compression structure 240. Then compression structure 240 repeatedly compresses and releases their chest. These compressions and releases are designated by arrow 248, regardless of how effectuated. Note that the arrow 248 indicates that the compressions are in the center of the patient's chest.

Compression structure 240 is shown as reaching around the chest of patient 282. This alleviates a problem of the patient being on a flexible mattress, which causes ineffective CPR. Indeed, compressions 248 are with respect to compression structure 240, not the mattress. But structure 240 typically does not cover, for example, the head of patient 282.

Compression structure 240 is abstracted, in that it may be implemented in any number of ways. In some embodiments, a belt squeezes and releases the patient's chest.

The compression structure 240 utilizes the disclosed UWB technology to determine a depth of compression for CPR chest compressions. In one or more implementations, UWB technology determines the depth of a CPR compression delivered by the compression structure 240. For example, a system for determining the depth of chest compressions includes an adjunct 250 (example, a pressure plate or a suction cup, etc., depending on the type of CPR machine) that is positioned near the patient's chest, a processor 258, and a constellation 260 of one or more UWB units fixed into part of a backboard 262. The processor 258 causes the UWB units of the constellation 260 to transmit UWB signals (of different wavelengths, for example, so that each UWB unit's UWB signal can distinguished), causing the adjunct to reflect the signal back into the direction of the UWB units. The processor 258 collects the time measurements from each UWB unit and determines therefrom the distance many times per second to detect the motion of the adjunct 250 (relative to the constellation) during chest compression.

In one or more implementations, UWB technology determines the depth of a CPR compression based, at least in part, upon two points. One point is relative to the patient's chest and another point is relative the patient's back. These points are illustrated in FIG. 2 as front point 270 and back point 272. More particularly, the adjunct 250 is designed to be in a fixed spatial relation with the front point and/or the back point while the other of the tag or the antenna is designed to be in a fixed spatial relation with the other of the tag and the antenna.

To illustrate, the compression structure 240 includes the adjunct 250, which is in proximity to the chest of the patient 282. In one or more implementations, the adjunct 250 is adhered to the chest of the patient 282.

In FIG. 2, there is an exaggerated gap between the patient's chest and the top of the compression structure 240. In reality and in other implementations, there may be little to no gap.

The compression structure 240 is coupled to processor 258. In this way, the processor 258 is coupled to the adjunct 250 and the constellation 260. The adjunct 250 reflects the UWB signals transmitted by the constellation 260. The UWB units of the constellation receive the reflections of their respective UWB signal and determine a time for the "round trip" to and from the adjunct, from which the processor 258 can determine a distance of the front point 270 to the back point 272.

When compressions 248 are performed on the patient 282, the adjunct 250 moves from a position 252 to a position 254. The distance that the adjunct 250 travels when it moves from position 252 to position 254 is correlated to a depth of compression.

Based at least in part on the time measurements from the UWB units in constellation 260, the processor 258 can determine the depth of the compressions 248 during delivery of the CPR chest compression.

In one or more implementations, the adjunct 250 is disposable or reusable. Alternatively, the adjunct 250 can be encapsulated into extremely durable reusable configurations.

Figure 3:
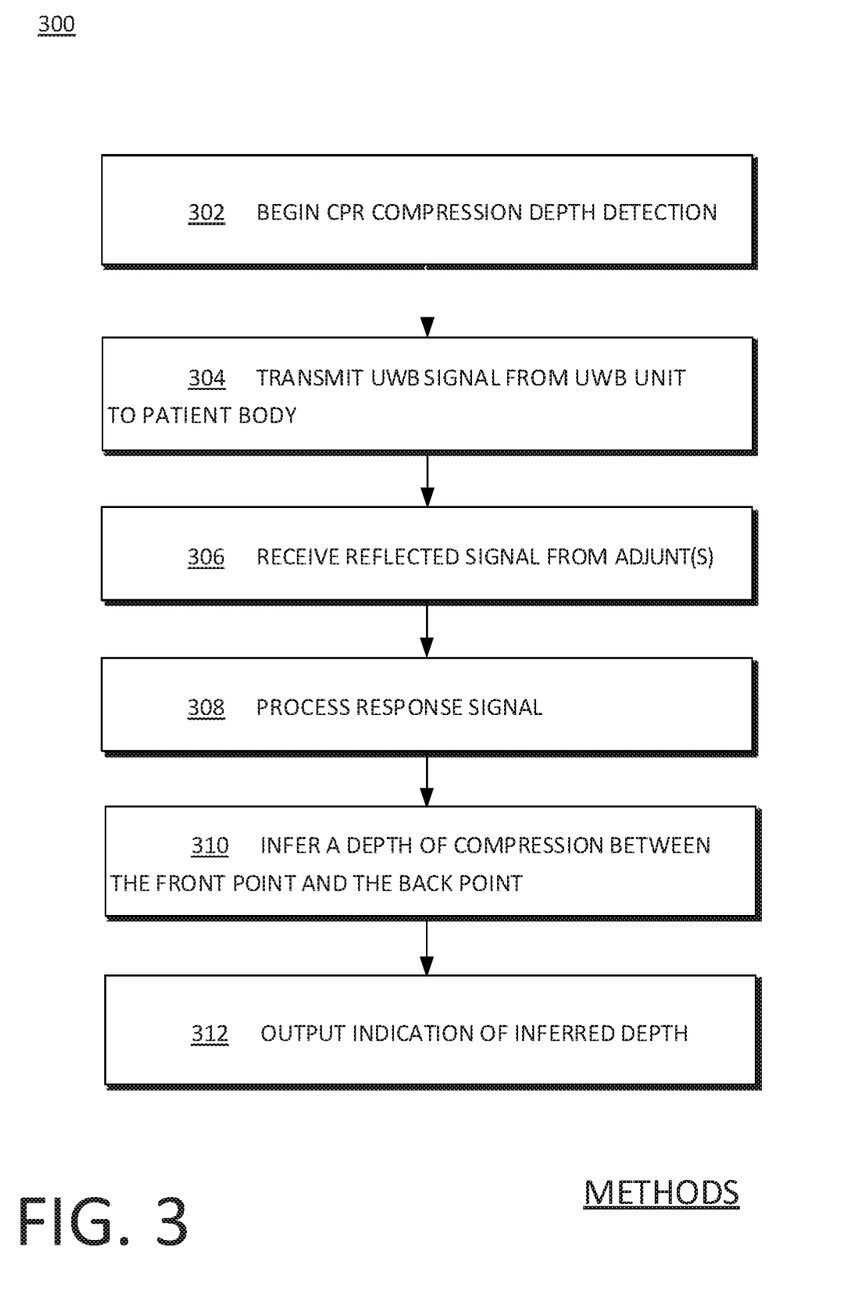
FIG. 3 is a flowchart for illustrating methods of determining CPR compression depth according to embodiments.

FIG. 3 shows a flowchart 300 for describing methods according to embodiments, to deliver CPR compressions to a patient. The method of flowchart 300 may be practiced by CPR chest compression machines or by a standalone device. For instance, the external CPR chest compressor includes a processor, which is coupled to one or more UWB units. One or more adjuncts are arranged in proximity to the patient's chest. The CPR chest compression includes a first depth of compression.

According to an operation 302, a CPR chest compression occurs. It occurs between a front point that corresponds to a chest of the patient and a back point that corresponds to a back of the patient.

According to an operation 304, the UWB unit(s) transmits a UWB signal into the patient's body. In one embodiment, the UWB signal(s) are transmitted toward the adjunct(s), which can then reflect the UWB signal(s) back toward the UWB units.

An operation 306 receives reflected UWB signal(s) from the adjunct(s). In one embodiment, the UWB units receive the reflected signals.

An operation 308 processes the reflected UWB signal(s). In one embodiment, the UWB unit(s) measure the round trip time for the UWB signal to reach the adjunct(s) and return to the UWB unit(s). Then the processor receives the time measurements and determines a position of the adjunct relative to the UWB unit(s).

An operation 310, based at least in part upon the reflected UWB signal(s), infers a depth of compression between the front point and the back point.

An operation 312 outputs an indication of the inferred depth of compression. The indication can be used by a rescuer so as to adjust how deeply the rescuer is compressing and/or releasing the patient's chest while performing CPR.

For flowchart 300, it will be recognized that a number of their operations can be augmented with what was described above. For example, in light of this disclosure, one of skill in the art will appreciate that the UWB unit(s) may be arranged in proximity to the front point and the adjuncts in proximity to the back point (e.g. on the patient's back, on a CPR machine backboard, on a stretcher upon which the patient is place in a supine position, etc.)

Figure 4:
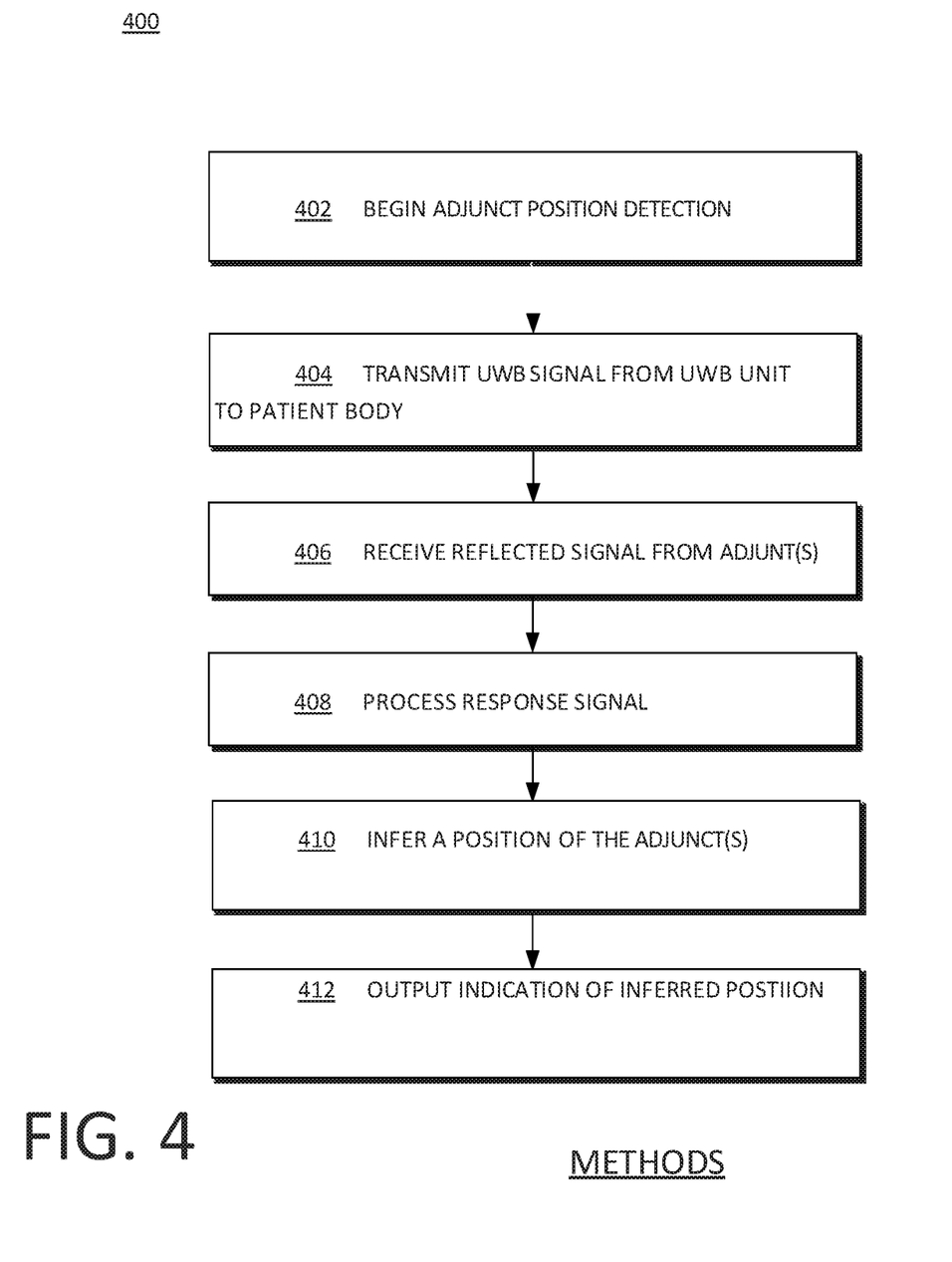
FIG. 4 is a flowchart for illustrating methods of determining adjunct(s) position(s) according to embodiments.

FIG. 4 shows a flowchart 400 for describing methods according to embodiments, to determine the position of adjuncts on a patient. The method of flowchart 400 may be practiced by a defibrillator, a CPR chest compression machines or by other standalone medical devices. For instance, in one embodiment, an external CPR chest compressor includes a processor, which is coupled to one or more UWB units. One or more adjuncts are arranged in proximity to the patient's chest. In this application, the position of the adjuncts is detected to ensure the adjunct(s) is properly positioned on the patient.

According to an operation 402, one or more adjuncts are positioned on a patient's body.

According to an operation 404, the UWB unit(s) transmits a UWB signal into the patient's body. In one embodiment, the UWB signal(s) are transmitted toward the adjunct(s), which can then reflect the UWB signal(s) back toward the UWB units.

An operation 406 receives reflected UWB signal(s) from the adjunct(s). In one embodiment, the UWB unit(s) receives the reflected UWB signals.

An operation 408 processes the reflected UWB signal(s). In one embodiment, the UWB unit(s) measure the round trip time for the UWB signal to reach the adjunct(s) and return to the UWB unit(s). Then the processor receives the time measurements and determines a position of the adjunct relative to the UWB unit(s).

An operation 410, based at least in part upon the reflected UWB signal(s), infers a position of the adjunct(s) on the patient's body.

An operation 412 outputs an indication of the inferred position(s). The indication can be used by a rescuer so as to adjust the position of the adjunct.

For flowchart 400, it will be recognized that a number of their operations can be augmented with what was described above. For example, in light of this disclosure, one of skill in the art will appreciate that the UWB unit(s) may be arranged in proximity to the front point and the adjuncts in proximity to the back point (e.g. on the patient's back, on a CPR machine backboard, on a stretcher upon which the patient is place in a supine position, etc.)

Figure 5:
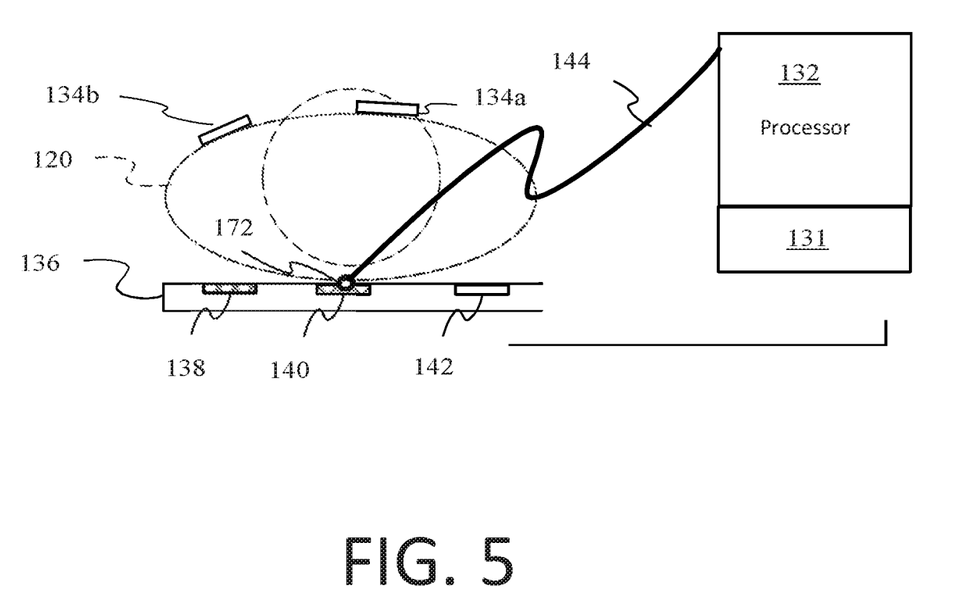
FIG. 5 is a diagram of an abstracted system capable of practicing the method of FIG. 4, according to an embodiment.

FIG. 5 illustrates an example system capable of practicing the method 400 of FIG. 4. The elements of the system in FIG. 5 that have the same reference numerals as in FIG. 1 have similar structure and function. In this particular embodiment, adjuncts 134a and 134b are illustrated in different positions than adjunct 134 (FIG. 1), and wires 144 are illustrated as being connected to UWB units 138, 140 and 142 instead of adjunct 134 (FIG. 1).

When determining the adjunct positions, in this embodiment processor 132 causes UWB units 138, 140, and 142 to transmit UWB signals of different wavelength toward the adjuncts 134a and 134b. As previously described for other embodiments, the adjuncts reflect the UWB signals and the UWB units can measure the round trip time for the UWB signal to reach the adjunct(s) and return to the UWB units after reflection. The processor 132 can process these times and determine a position of the adjunct(s), for example by using triangulation techniques.

CPR backboards are routinely used to help facilitate CPR anytime the patient is situated on a compliant surface, such as a stretcher, gurney, or hospital bed. Some embodiments involve incorporating the electronics for one or more UWB units into a CPR backboard, such that the embedded electronics are flush with the top and bottom surfaces of the back board, and are positioned such that they would lie approximately under the sternum of the patient when the board is appropriately placed beneath the patient.

In one embodiment the backboard may be designed using a single UWB unit, implemented in a manner (such as a phased-array) that would allow it to determine distance and angle to a target point on or in the patient's chest.

Once the phantom-containing adjunct is placed on or in the patient, the UWB unit(s) would identify and track the direction and distance between the backboard and the phantom, thus providing information on the presence and relative or absolute location of those adjuncts. Such information could be recorded by the backboard containing the UWB unit(s), and could additionally be relayed in a wired or wireless fashion to an associated monitor/defibrillator. The monitor/defibrillator could then provide appropriate feedback, guidance, and alarms based on that information.

Options for the phantom include being incorporated in to Defibrillation pads. Existing defibrillation pads may already be sufficiently and distinctly reflective to RF. However, they could be further adapted by: Enhancing the reflectivity with an additional reflective layer embedded into the pad; Adding a unique reflective pattern to the pad, to aid in distinguishing the target pads from other reflective aspects of the environment, and also possibly distinguishing each pad from each other.

Other embodiments can be adapted for endotracheal tubes. Endotracheal tubes could be adapted to incorporate a distinguishable phantom at the distal end of the tube.

Still other embodiments can be adapted for Mechanical chest compression devices. For example, the piston of the aforementioned LUCAS device could be modified to make it sufficiently RF reflective. The LUCAS device could also be adapted to mount onto the UWB-containing backboard, rather than its standard backboard. The LUCAS device could also be adapted to incorporate one or more UWB units in its standard backboard.

Application/use scenarios include a monitor/defibrillator that could gain awareness of the position of the defibrillation pads. If the pads are too close together, or not oriented at reasonable angles/directions relative to the backboard, the monitor/defibrillator could: Advise the user to correct/improve the positioning of the pads; Only provide such advice if defibrillation is attempted; Further restrict provision of such advice to situations where defibrillation is attempted, and the monitor/defibrillator—via use of a rhythm analysis algorithm—determines that defibrillation was unsuccessful.

In a further enhancement, the monitor/defibrillator could record the pad position information for later analysis. The UWB system might also be able to distinguish the patient's ribs and sternum, and could additionally use a map of the skeletal structure of the patient's chest to enhance interpretation of the location of the pads.

If a mechanical chest compression device such as LUCAS is additionally used during the resuscitation, the monitor/defibrillator could additionally incorporate knowledge of the location of the LUCAS piston to enhance interpretation of the location of the pads.

If a mechanical chest compression device such as LUCAS is additionally used during the resuscitation, the monitor/defibrillator could identify changes in the relationship between the location of the LUCAS piston and the defibrillation pads, which would be indicative of sliding/slipping of the LUCAS on the patient's chest, which is undesirable and potentially harmful.

Upon such identification, the monitor/defibrillator could: advise/warn the user to readjust the LUCAS device; and/or automatically communicate to the LUCAS device to halt compressions, until it is repositioned and then restarted by the user.

If the LUCAS backboard incorporated the UWB system, the above could be accomplished without needing a monitor/defibrillator in the communication loop.

A monitor/defibrillator could gain awareness of when intubation has been completed, via detection of the endotracheal tube phantom within the field of view of the UWB unit. With this awareness, the monitor/defibrillator could: Log the time for later documentation, QA review, and interpretation of other data collected during the resuscitation.

The monitor/defibrillator could also alter the mode of any features that are airway-status dependent, including: metronome or other guidance surrounding C:V patterns; the displayed screen content, such as the choice and ordering of waveforms and monitoring parameter information; and/or alarm behavior.

In the above description of exemplary implementations, for purposes of explanation, specific numbers, materials configurations, and other details are set forth in order to better explain the present invention, as claimed. However, it will be apparent to one skilled in the art that the claimed invention may be practiced using different details than the exemplary ones described herein. In other instances, well-known features are omitted or simplified to clarify the description of the exemplary implementations.

The inventors intend the described exemplary implementations to be primarily examples. The inventor does not intend these exemplary implementations to limit the scope of the appended claims. Rather, the inventor has contemplated that the claimed invention might also be embodied and implemented in other ways, in conjunction with other present or future technologies.

Moreover, the word "exemplary" is used herein to mean serving as an example, instance, or illustration. Any aspect or design described herein as exemplary is not necessarily to be construed as preferred or advantageous over other aspects or designs. Rather, use of the word "exemplary" is intended to present concepts and techniques in a concrete fashion. The term "technology," for instance, may refer to one or more devices, apparatuses, systems, methods, articles of manufacture, and/or computer-readable instructions as indicated by the context described herein.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

Note that the order in which the processes are described is not intended to be construed as a limitation, and any number of the described process blocks can be combined in any order to implement the processes or an alternate process. Additionally, individual blocks may be deleted from the processes without departing from the spirit and scope of the subject matter described herein.

One or more embodiments described herein may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "computer-readable media" includes computer-storage media. For example, computer-storage media may include, but are not limited to, magnetic storage devices (e.g., hard disk, floppy disk, and magnetic strips), optical disks (e.g., compact disk [CD] and digital versatile disk [DVD]), smart cards, flash memory devices (e.g., thumb drive, stick, key drive, and SD cards), and volatile and nonvolatile memory (e.g., RAM and ROM).

In the claims appended herein, the inventor invokes 35 U.S.C. § 112, paragraph 6 only when the words "means for" or "steps for" are used in the claim. If such words are not used in a claim, then the inventor does not intend for the claim to be construed to cover the corresponding structure, material, or acts described herein (and equivalents thereof) in accordance with 35 U.S.C. § 112, paragraph 6.

What is claimed is:

1. A defibrillator, comprising:
   transmitters configured to transmit ultra-wide band (UWB) signals into a patient;
   defibrillation pads configured to be disposed on the patient and to reflect the UWB signals;
   receivers configured to receive the UWB signals that have been reflected by the defibrillation pads;
   an output device;
   a processor; and
   memory storing instructions that, when executed by the processor, cause the processor to perform operations comprising:

determining times-of-flight of the UWB signals between the transmitters and the receivers;

determining positions of the defibrillation pads based on the times-of-flight of the UWB signals; and causing the output device to output an instruction to change the positions of the defibrillation pads.

2. The defibrillator of claim 1, wherein determining the positions of the defibrillation pads based on the time-of-flights of the UWB signals comprises:

determining distances between the transmitters, the defibrillation pads, and the receivers based on the times-of-flight;

identifying positions of the transmitters and the receivers; and triangulating the positions of the defibrillation pads based on the distances and the positions of the transmitters and the receivers.

3. The defibrillator of claim 1, wherein the transmitters and the receivers are located on a backboard.

4. A defibrillator, comprising:

a transmitter configured to wirelessly transmit a signal into a patient;

a defibrillation pad configured to be disposed on the patient and configured to reflect the signal;

a receiver configured to receive the signal that has been reflected by the defibrillation pad;

an output device;

a processor; and memory storing instructions that, when executed by the processor, cause the processor to perform operations comprising:

determining a time-of-flight of the signal between the transmitter and the receiver;

determining a position of the defibrillation pad based on the time-of-flight of the signal; and causing the output device to output an indication of the position of the defibrillation pad.

5. The defibrillator of claim 4, wherein the signal comprises a radio frequency (RF) signal.

6. The defibrillator of claim 5, wherein the signal comprises an ultra-wide band (UWB) signal.

7. The defibrillator of claim 4, wherein the transmitter and the receiver are comprised in a backboard.

8. The defibrillator of claim 4, further comprising:

a circuit configured to output a defibrillation shock to the defibrillation pad, wherein the operations further comprise:

causing the circuit to output the defibrillation shock; and in response to causing the circuit to output the defibrillation shock, detecting a heart rhythm of the patient, and wherein determining the time-of-flight is in response to detecting the heart rhythm of the patient.

9. The defibrillator of claim 8, wherein the operations further comprise:

causing the output device to output an instruction to change the position of the defibrillation pad.

10. The defibrillator of claim 4, wherein the defibrillation pad comprises a metal film that is configured to reflect the signal.

11. The defibrillator of claim 4, wherein the defibrillation pad comprises a material that is configured to modify a spectral signature of the signal.

12. The defibrillator of claim 4, wherein the defibrillation pad comprises a metallic pattern that is configured to reflect the signal.

13. A method, comprising:

wirelessly transmitting, by a transmitter and into a patient, a signal that is reflected by a defibrillation pad;

receiving, by a receiver, the signal;

determining a time-of-flight of the signal between the transmitter and the receiver;

determining a position of the defibrillation pad based on the time-of-flight of the signal; and outputting, by an output device, an indication of the position of the defibrillation pad.

14. The method of claim 13, wherein the signal comprises a radio frequency (RF) signal.

15. The method of claim 14, wherein the signal comprises an ultra-wide band (UWB) signal.

16. The method of claim 13, further comprising:

outputting a defibrillation shock to the defibrillation pad; and in response to outputting the defibrillation shock, detecting a heart rhythm of the patient, wherein determining the time-of-flight is in response to detecting the heart rhythm of the patient.

17. The method of claim 13, further comprising:

outputting, by the output device, an instruction to change the position of the defibrillation pad.

18. The method of claim 13, wherein the defibrillation pad comprises a metal film that is configured to reflect the wireless signal.

19. The method of claim 13, further comprising:

in response to receiving the signal, determining, based on a spectral signature of the signal, that the signal was reflected from the defibrillation pad.

* * * * *